(12) United States Patent
Sinderby et al.

(10) Patent No.: US 10,758,693 B2
(45) Date of Patent: Sep. 1, 2020

(54) METHOD AND SYSTEM FOR ADJUSTING A LEVEL OF VENTILATORY ASSIST TO A PATIENT

(71) Applicant: ST. MICHAEL'S HOSPITAL, Toronto (CA)

(72) Inventors: Christer Sinderby, Toronto (CA); Jennifer Beck, Toronto (CA); Norman Comtois, Scarborough (CA); Fredrik Jalde, Sundbyberg (SE)

(73) Assignee: St. Michael's Hospital., Toronto, Ontario (CA)

( * ) Notice: Subject to any disclaimer, the term of this patent is extended or adjusted under 35 U.S.C. 154(b) by 630 days.

(21) Appl. No.: 15/261,532

(22) Filed: Sep. 9, 2016

(65) Prior Publication Data

US 2017/0128684 A1 May 11, 2017

Related U.S. Application Data

(60) Provisional application No. 62/216,696, filed on Sep. 10, 2015.

(51) Int. Cl.
*A61M 16/20* (2006.01)
*A61M 16/00* (2006.01)

(52) U.S. Cl.
CPC ......... *A61M 16/024* (2017.08); *A61M 16/204* (2014.02); *A61M 2016/0027* (2013.01);
(Continued)

(58) Field of Classification Search
CPC ..... A61B 5/0205; A61B 5/0836; A61B 5/087; A61B 5/091; A61B 5/7264; A61B 5/7267;
(Continued)

(56) References Cited

U.S. PATENT DOCUMENTS

| 4,155,356 A * | 5/1979 | Venegas | A61M 16/022 128/204.23 |
| 5,316,009 A * | 5/1994 | Yamada | A61B 5/087 128/204.23 |

(Continued)

FOREIGN PATENT DOCUMENTS

| EP | 1 068 875 | 9/2010 |
| EP | 1 896 102 | 2/2012 |

(Continued)

*Primary Examiner* — Annette Dixon
(74) *Attorney, Agent, or Firm* — Fay Kaplun & Marcin, LLP

(57) ABSTRACT

The present disclosure relates to a method and a mechanical ventilation system for adjusting a level of ventilatory assist to a patient. A neuro-mechanical efficiency of the patient is determined. A control value is received at the mechanical ventilation system. The level of ventilatory assist to the patient is determined on the basis of the neuro-mechanical efficiency and of the control value. The mechanical ventilation system may be adjusted automatically based on the determined level of ventilatory assist to the patient. Alternatively, the determined level of ventilatory assist to the patient may be displayed for the benefit of an operator and a manual command may be received for adjusting the mechanical ventilation system.

32 Claims, 9 Drawing Sheets

(52) U.S. Cl.
CPC ............... *A61M 2016/0036* (2013.01); *A61M 2205/3569* (2013.01); *A61M 2205/3592* (2013.01); *A61M 2205/502* (2013.01); *A61M 2230/60* (2013.01)

(58) Field of Classification Search
CPC .............. A61M 16/00; A61M 16/0006; A61M 16/0009; A61M 16/0051; A61M 16/0057; A61M 16/0063; A61M 16/0069; A61M 16/0075; A61M 16/022; A61M 16/026; A61M 16/04; A61M 16/0666; A61M 16/0816; A61M 16/0833; A61M 16/0858; A61M 16/0875; A61M 16/12; A61M 2016/0021; A61M 2016/0027; A61M 2016/003; A61M 2016/0033; A61M 2016/0036; A61M 2016/0039; A61M 2016/0042; A61M 2205/15; A61M 2205/3344; A61M 2205/3553; A61M 2205/505; A61M 2205/8206; A61M 2230/005; A61M 2230/04; A61M 2230/06; A61M 2230/205; A61M 2230/30; A61M 2230/432; A61M 2230/435; A61M 2230/46; A61M 2230/50; G06F 19/3456; G06F 19/3481; G16H 40/63; Y10S 128/924; Y10S 128/925
See application file for complete search history.

(56) References Cited

U.S. PATENT DOCUMENTS

| | | | |
|---|---|---|---|
| 5,671,752 A | 9/1997 | Sinderby et al. | |
| 6,253,765 B1 | 7/2001 | Hognelid et al. | |
| 6,390,091 B1* | 5/2002 | Banner | A61M 16/0051 |
| | | | 128/202.22 |
| 6,796,305 B1* | 9/2004 | Banner | A61B 5/0205 |
| | | | 128/204.21 |
| 6,840,240 B1* | 1/2005 | Berthon-Jones | A61M 16/00 |
| | | | 128/204.18 |
| 7,021,310 B1 | 4/2006 | Sinderby et al. | |
| 8,267,085 B2* | 9/2012 | Jafari | A61M 16/0051 |
| | | | 128/202.22 |
| 8,469,027 B2* | 6/2013 | Choncholas | A61B 5/091 |
| | | | 128/200.24 |
| 8,551,009 B2 | 10/2013 | Sinderby | |
| 8,720,441 B2 | 5/2014 | Sinderby | |
| 9,949,661 B2* | 4/2018 | Eger | A61B 5/0004 |
| 2003/0159695 A1* | 8/2003 | Younes | A61M 16/00 |
| | | | 128/204.18 |
| 2011/0301482 A1 | 12/2011 | Sinderby et al. | |
| 2012/0103334 A1 | 5/2012 | Sinderby | |
| 2015/0059752 A1* | 3/2015 | Bellani | A61M 16/0003 |
| | | | 128/204.23 |
| 2015/0265833 A1* | 9/2015 | Meyyappan | A61B 5/08 |
| | | | 128/204.21 |
| 2018/0199846 A1* | 7/2018 | Eger | A61B 5/0004 |

FOREIGN PATENT DOCUMENTS

| | | |
|---|---|---|
| WO | 1998/48877 | 11/1998 |
| WO | 1999/62580 | 12/1999 |
| WO | 2006/131149 | 12/2006 |
| WO | 2008/131798 | 11/2008 |
| WO | 2010/081230 | 7/2010 |
| WO | 2015/089668 | 6/2015 |
| WO | 2016/089668 | 6/2015 |
| WO | 2016/153406 | 9/2016 |

* cited by examiner

METHOD AND SYSTEM FOR ADJUSTING A LEVEL OF VENTILATORY ASSIST TO A PATIENT

TECHNICAL FIELD

The present disclosure relates to the field of ventilatory assist to a patient. More specifically, the present disclosure relates to a method and system for adjusting a level of ventilatory assist to a patient.

BACKGROUND

Mechanical ventilators are used to assist or replace at least in part spontaneous breathing of a patient. Although significant advances have been made in ventilation therapy, it is still difficult a task to determine the level of ventilatory assist that may be required, at any given time, by a patient.

U.S. Pat. No. 8,720,441 B2 to Sinderby, issued on May 13, 2014, the full disclosure of which is incorporated by reference herein, describes how a patient's efficiency to generate an inspiratory volume without mechanical ventilatory assist and a patient's efficiency to generate an inspiratory volume with mechanical ventilatory assist are calculated and used to determine a patient-ventilator breath contribution index. This reference expresses that a patient-ventilator breath contribution is related to a relative unloading of the respiratory muscles. The relative unloading may be expressed as a reduction, in percentage, of inspiratory oesophageal pressure variations obtained through the use of mechanical ventilatory assist.

US Patent Application Publication 2001/0301482 A1 to Sinderby et al., published on Dec. 8, 2011, the full disclosure of which is incorporated by reference herein, describes a method and a system for measuring changes in inspiratory load of a patient's respiratory system during mechanical ventilation. The method and system calculate a first relation between a measured inspiratory airway pressure and a measured electrical activity of respiratory muscle, and a second relation between a measured inspiratory volume and the measured electrical activity. A load index is calculated from the first and second relations. Changes in inspiratory load are determined based on the load index.

The above references and other known techniques that provide information feedback related to a patient's respiratory system are instrumental in controlling mechanical ventilators. However, they still fail to provide readily usable ventilatory assist level information, for example a numerical value indicative of the level of ventilatory assist to be applied to a certain patient.

Therefore, there is a need for technical solutions providing ventilatory assist level information readily usable for adjusting the level of ventilatory assist to a patient.

SUMMARY

According to the present disclosure, there is provided a method implemented in a mechanical ventilation system for adjusting a level of ventilatory assist ASSIST to a patient, comprising: receiving a control value at the mechanical ventilation system; determining a neuro-mechanical efficiency NME of the patient; and determining the level of ventilatory assist ASSIST to the patient on the basis of the neuro-mechanical efficiency NME and of the control value.

According to the present disclosure, there is also provided a mechanical ventilation system for adjusting a level of ventilatory assist ASSIST to a patient, comprising: an operator interface adapted to receive a control value; a detector of a neuro-mechanical efficiency NME of the patient; and a controller of the level of ventilatory assist ASSIST to the patient responsive to the control value from the operator interface and to the neuro-mechanical efficiency NME from the detector to determine the level of ventilatory assist ASSIST to the patient on the basis of the neuro-mechanical efficiency NME and of the control value.

The foregoing and other features will become more apparent upon reading of the following non-restrictive description of illustrative embodiments thereof, given by way of example only with reference to the accompanying drawings.

BRIEF DESCRIPTION OF THE DRAWINGS

Embodiments of the disclosure will be described by way of example only with reference to the accompanying drawings, in which.

Like numerals represent like features on the various figures of drawings.

DETAILED DESCRIPTION

Various aspects of the present disclosure generally address and solve one or more of the problems related to a lack of ventilatory assist level information, for example a numerical value indicative of the level of ventilatory assist to be applied to a certain patient, which ventilatory assist level information being readily usable for adjusting the level of ventilatory assist to a patient.

Using the technology described in the present disclosure, a mechanical ventilation system determines a level of ventilatory assist that reflects the actual needs of a patient. Based on this determination, the mechanical ventilation system may be adjusted automatically. Alternatively, the determined level of ventilatory assist may be presented on a display for the benefit of an operator, or caregiver, who may in turn provide a command for manually adjusting the mechanical ventilation system.

To this end, a neuro-mechanical efficiency of the patient is determined using patient's airway pressure and respiratory muscle electrical activity (neural activity) measurements obtained while causing a patient's inspiratory occlusion.

The level of ventilatory assist to the patient is determined on the basis of the neuro-mechanical efficiency and of a control value specified by the operator or caregiver and received at the mechanical ventilation system.

In one embodiment, the specified control value is a target electrical activity of the patient's respiratory muscle synchronized with an inspiratory effort for a normally breathing patient. In another embodiment, the specified control value is a setting for a variation of the patient's airway pressure. In a further embodiment, the specified control value is a desired unloading level for the patient. In yet another embodiment, the control value is a target tidal volume for the patient.

Figure 1:
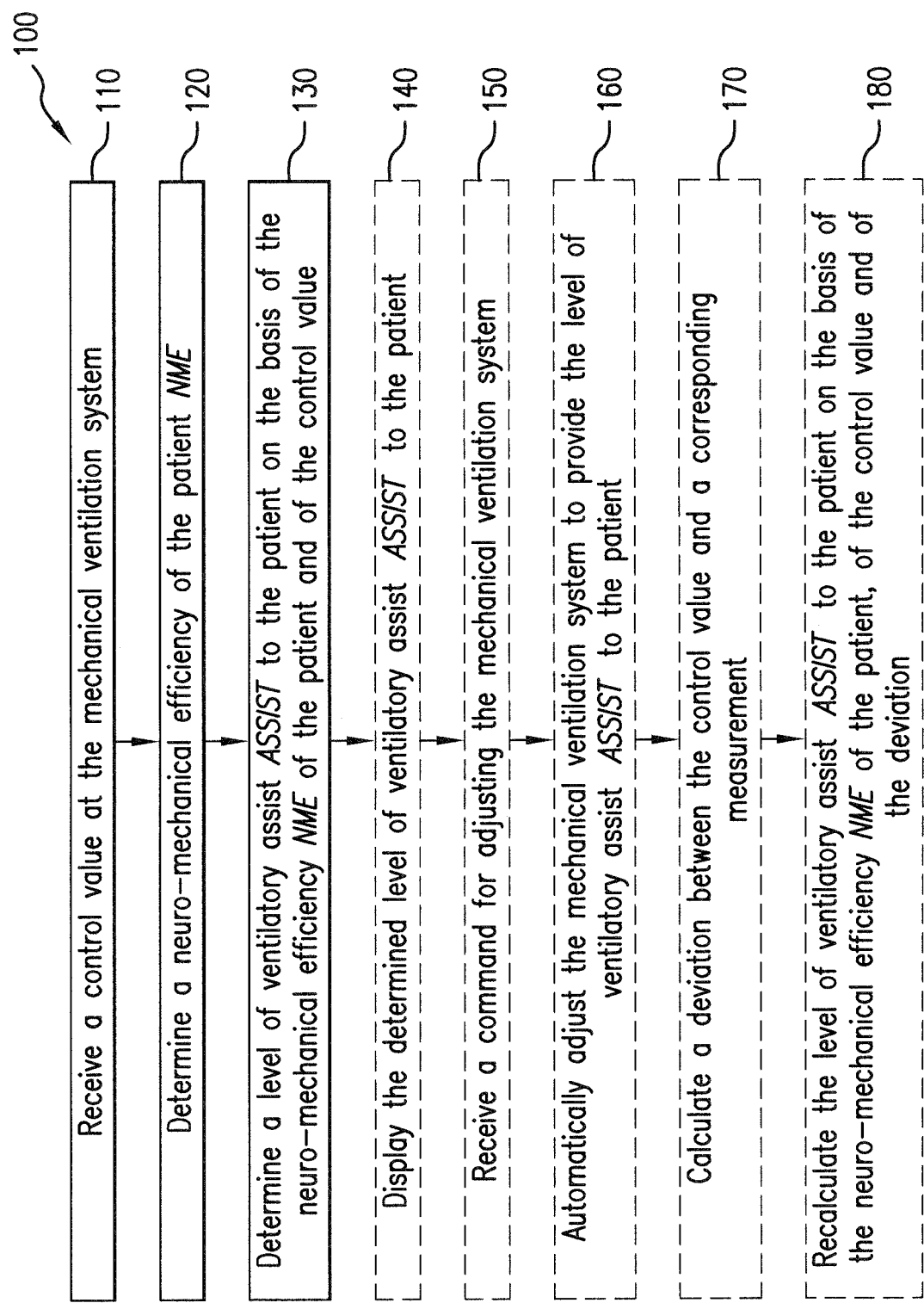
FIG. 1 illustrates a flow chart showing operations of a method implemented in a mechanical ventilation system for determining and adjusting a level of ventilatory assist to a patient according to an embodiment.

Referring now to the drawings, FIG. 1 illustrates a flow chart showing operations of a method implemented in a mechanical ventilation system for determining and adjusting a level of ventilatory assist to a patient according to an embodiment. The flow chart of FIG. 1 includes a sequence 100 comprising a plurality of operations that may be executed in variable order, some of the operations possibly being executed concurrently, some of the operations being optional. The sequence 100 comprises the following operations:

Operation 110: A control value specified by an operator or by a caregiver is received at the mechanical ventilation system. This value may be specified before or during the provision of mechanical ventilation to the patient, and may be provided once, or modified over time by the operator based on the evolution of the condition of the patient.

Operation 120: A neuro-mechanical efficiency NME of the patient is determined.

Operation 130: A level of ventilatory assist ASSIST to the patient is determined on the basis of the neuro-mechanical efficiency NME of the patient and of the control value.

Operation 140: The determined level of ventilatory assist ASSIST may optionally be displayed on a display for the benefit of an operator or caregiver.

Operation 150: Optionally, a command may be received for adjusting the mechanical ventilation system.

Operation 160: Optionally, the mechanical ventilation system may be automatically adjusted to provide the level of ventilatory assist ASSIST to the patient.

In an embodiment, the sequence 100 may be supplemented by the addition of a feedback loop acting upon a difference between the control value specified by the operator or caregiver and a related measurement. The feedback loop may comprise the following operations:

Operation 170: A deviation between the control value and a corresponding measurement is calculated.

Operation 180: The level of ventilatory assist ASSIST to the patient is recalculated on the basis of the neuro-mechanical efficiency NME of the patient, of the control value and of the deviation.

Optional operations 140 and 150, or optional operation 160, may be executed again.

The feedback loop may, for example, be based on a proportional-integral-derivative control operation. As a non-limitative example where the control value is a target electrical activity of a patient's respiratory muscle, an actual electrical activity measurement may show that an initial level of ventilatory assist ASSIST to the patient calculated at operation 130 is inadequate for meeting the target electrical activity level. Automatic or manual adjustment of the mechanical ventilation system according to the recalculated level of ventilatory assist ASSIST to the patient obtained at operation 180 may bring the measured electrical activity level closer to the target electrical activity specified by the operator. In an embodiment, operations 160, 170 and 180 may be repeated automatically until the control value specified at operation 110 is met.

Figure 2:
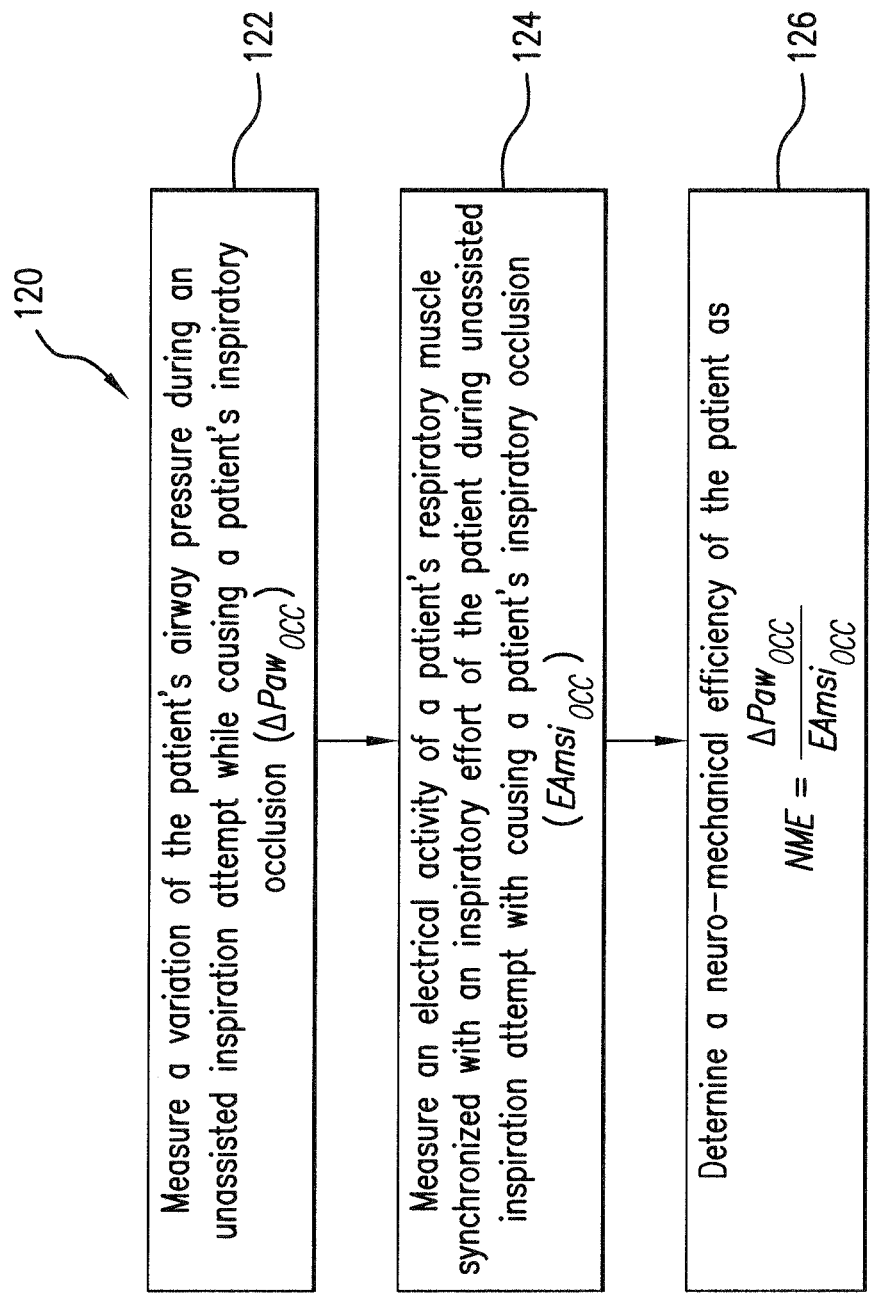
FIG. 2 illustrates a flow chart showing operations of a method implemented in a mechanical ventilation system for determining a neuro-mechanical efficiency of the patient.

FIG. 2 illustrates a flow chart showing operations of a method implemented in a mechanical ventilation system for determining a neuro-mechanical efficiency of the patient. Operation 120 for determining the neuro-mechanical efficiency NME of the patient may include the following sub-operations, which may be executed in variable order:

Operation 122: A variation of patient's airway pressure is measured during a patient's unassisted inspiration attempt while causing a patient's inspiratory occlusion. This variation of patient's airway pressure is identified by the term $\Delta Paw_{occ}$.

Operation 124: Electrical activity of a patient's respiratory muscle synchronized with an inspiratory effort of the patient during the patient's unassisted inspiration attempt while causing patient's inspiratory occlusion is measured. This electrical activity of the patient's respiratory muscle is identified by the term $EAmsi_{occ}$.

Operation 126: The neuro-mechanical efficiency NME of the patient is then calculated using equation (1):

$$NME = \frac{\Delta Paw_{occ}}{EAmsi_{occ}} \tag{1}$$

It may be noted that, in operation 126 and in any other calculation using patient's airway pressure variation, an absolute value of the airway pressure variation may be used if required to obtain a positive result. Other methods of calculating the neuro-mechanical efficiency NME are contemplated, including for example methods that relate the neuro-mechanical efficiency NME to a ratio between an airway pressure variation and a variation of the electrical activity of a patient's respiratory muscle. Further methods of calculating the neuro-mechanical efficiency NME, in which NME may be defined as the efficiency of the patient's respiratory system to generate inspiratory volume in response to electrical activity of the patient's diaphragm, are described in U.S. Provisional Patent Application 62/273,527 to Sinderby et al., filed on Dec. 31, 2015, the full disclosure of which is incorporated by reference herein.

Figure 3:
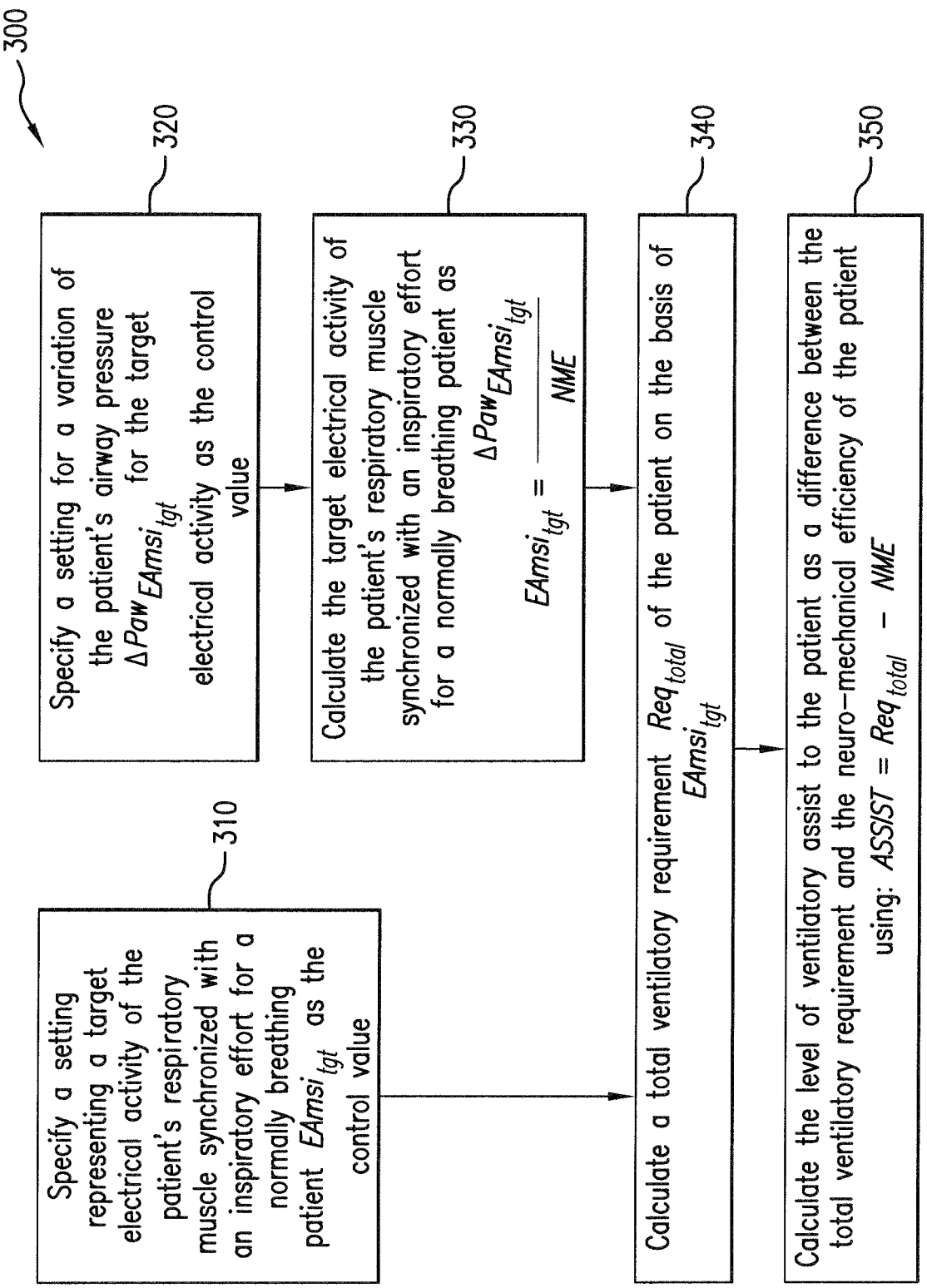
FIG. 3 illustrates a flow chart showing operations of a first method implemented in a mechanical ventilation system for calculating the level of ventilatory assist to the patient.

FIG. 3 illustrates a flow chart showing operations of a first method implemented in a mechanical ventilation system for calculating the level of ventilatory assist to the patient. The flow chart of FIG. 3 includes a sequence 300 comprising a plurality of operations that may be executed in variable order, some of the operations possibly being executed concurrently, some of the operations being optional. The sequence 300 comprises the following operations:

Operation 310: A setting representing a target electrical activity of the patient's respiratory muscle synchronized with an inspiratory effort for a normally breathing patient $EAmsi_{tgt}$ is specified as the value mentioned in the description of Operation 110, which is the control value.

Operation 320: As an alternative to operation 310, a setting for a variation of the patient's airway pressure $\Delta Paw_{EAmsi_{tgt}}$ for the target electrical activity is specified as the control value.

Operation 330: Following operation 320, the target electrical activity of the patient's respiratory muscle synchronized with an inspiratory effort for a normally breathing patient is calculated using equation (2):

$$EAmsi_{tgt} = \frac{\Delta Paw_{EAmsi_{tgt}}}{NME} \quad (2)$$

Operation 340: Whether $EAmsi_{tgt}$ is obtained through Operation 310 or through Operations 320 and 330, a total ventilatory requirement $Req_{total}$ of the patient is calculated on the basis of $EAmsi_{tgt}$.

Operation 350: The level of ventilatory assist to the patient mentioned in the description of Operation 230 is calculated as a difference between the total ventilatory requirement and the neuro-mechanical efficiency of the patient using equation (3):

$$ASSIST = Req_{total} - NME \quad (3)$$

Figure 4:
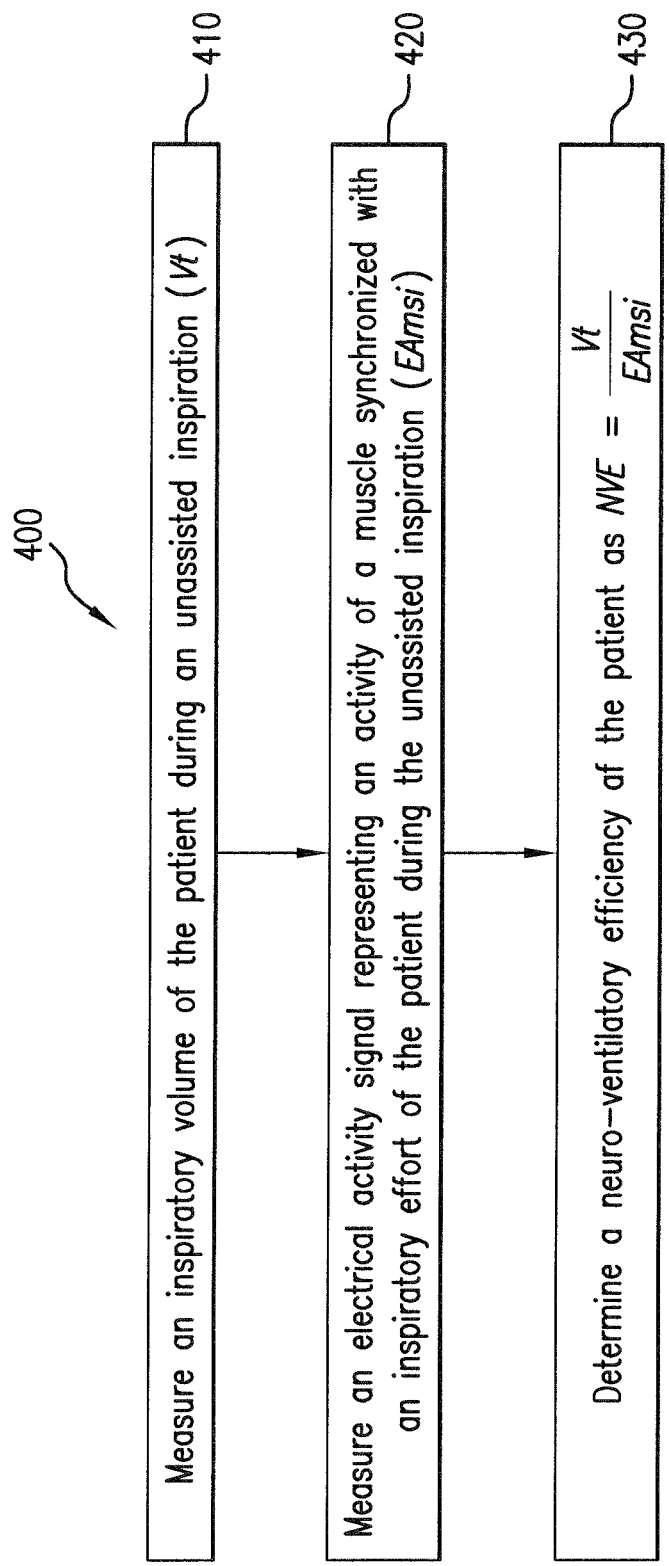
FIG. 4 illustrates a flow chart showing operations of a method implemented in a mechanical ventilation system for determining a neuro-ventilatory efficiency of the patient.

FIG. 4 illustrates a flow chart showing operations of a method implemented in a mechanical ventilation system for determining a neuro-ventilatory efficiency of the patient. The flow chart of FIG. 4 includes a sequence 400 comprising a plurality of operations that may be executed in variable order, some of the operations possibly being executed concurrently, some of the operations being optional. The sequence 400 comprises the following operations:

Operation 410: A patient's inspiratory volume Vt is measured during a patient's unassisted inspiration. The patient's inspiratory volume Vt is measured without patient's inspiratory occlusion.

Operation 420: Electrical activity of the patient's respiratory muscle synchronized with an inspiratory effort of the patient during the patient's unassisted inspiration is measured. This electrical activity of the patient's respiratory muscle is identified by the term EAmsi. The electrical activity EAmsi is measured without patient's inspiratory occlusion.

Operation 430: A neuro-ventilatory efficiency NVE of the patient is determined using equation (4):

$$NVE = \frac{Vt}{EAmsi} \quad (4)$$

Figure 5:
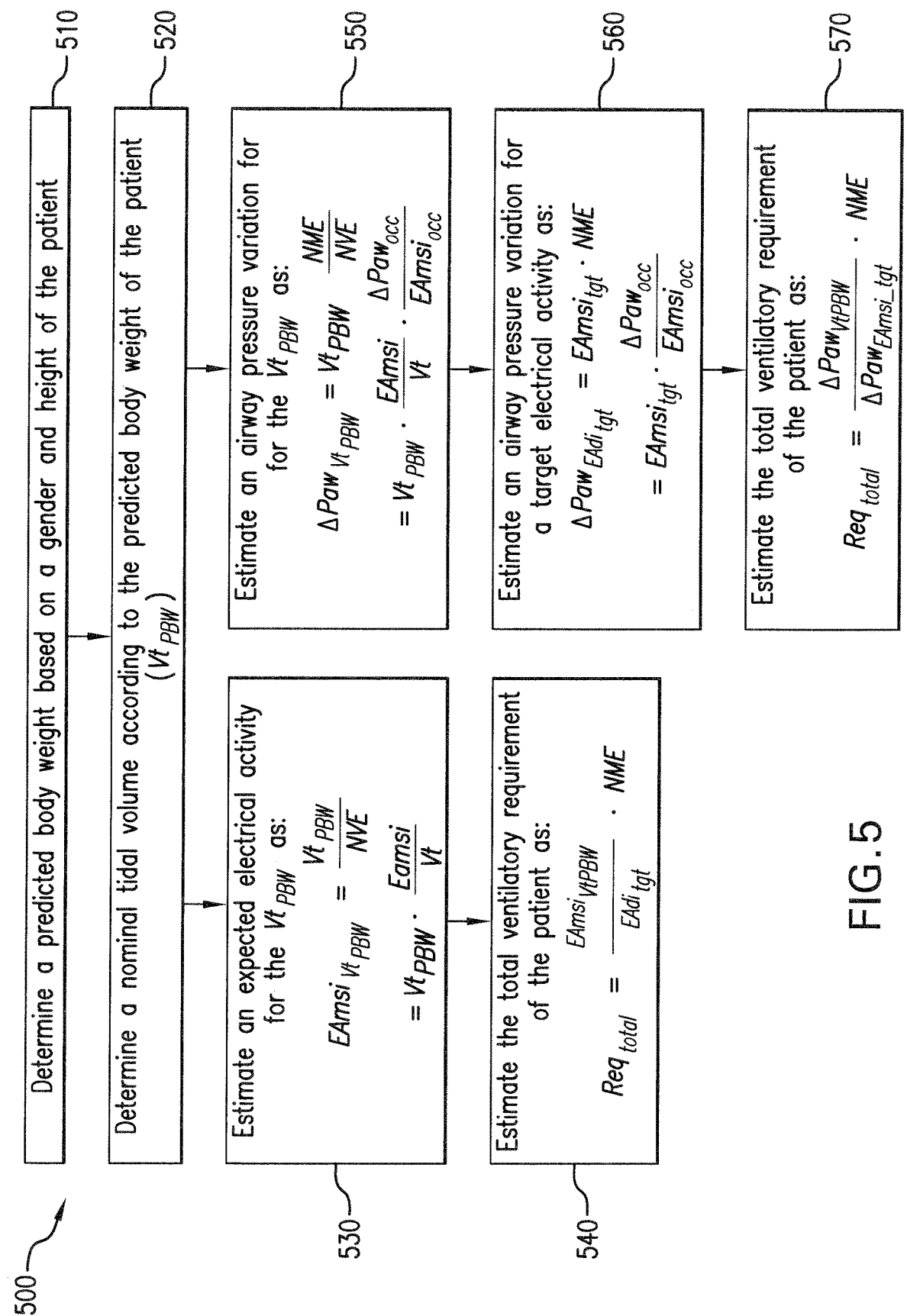
FIG. 5 illustrates a flow chart showing operations of a method implemented in a mechanical ventilation system for total ventilatory requirement of the patient.

FIG. 5 illustrates a flow chart showing operations of a method implemented in a mechanical ventilation system for total ventilatory requirement of the patient. The flow chart of FIG. 5 includes a sequence 500 comprising a plurality of operations that may be executed in variable order, some of the operations possibly being executed concurrently, some of the operations being optional. The sequence 500 comprises the following operations:

Operation 510: A predicted body weight PBW is determined based on a gender and height of the patient using, for example, tables according to well-known methods.

Operation 520: A nominal tidal volume $Vt_{PBW}$ is determined based on the predicted body weight PBW of the patient. The nominal tidal volume $Vt_{PBW}$ may for example be obtained by multiplying the predicted body weight PBW by a constant representative of an expected tidal volume per unit (for example per kg) of predicted body weight PBW, for example 6 ml per kg of predicted body weight PBW. Other well-known techniques for determining the nominal tidal volume $Vt_{PBW}$ may be implemented within the scope of the present disclosure.

Operation 530: An expected electrical activity $EAmsi_{Vt_{PBW}}$ of the patient's respiratory muscle is estimated based on the nominal tidal volume $Vt_{PBW}$ using equation (5):

$$EAmsi_{Vt_{PBW}} = \frac{Vt_{PBW}}{NVE} = Vt_{PBW} \cdot \frac{EAmsi}{Vt} \quad (5)$$

Operation 540: The operator or caregiver may provide a setting for a target electrical activity $EAmsi_{tgt}$ of the patient's respiratory muscle, which is a constant representative of the electrical activity of the patient's respiratory muscle synchronized with patient's inspiratory effort for a normally breathing patient, for example 10 µV when the patient's respiratory muscle is the diaphragm of the patient. Alternatively, the operator or caregiver may provide a setting for a variation of patient's airway pressure $\Delta Paw_{EAmsi_{tgt}}$ for the target electrical activity, in which case the target electrical activity $EAmsi_{tgt}$ of the patient's respiratory muscle may be calculated using equation (6):

$$EAmsi_{tgt} = \frac{\Delta Paw_{EAmsi_{tgt}}}{NME} \quad (6)$$

In either case, the total ventilatory requirement $Req_{total}$ of the patient is estimated at Operation 540 using equation (7):

$$Req_{total} = \frac{EAmsi_{Vt_{PBW}}}{EAmsi_{tgt}} \cdot NME \quad (7)$$

Alternatively, operations 530 and 540 may be replaced with the following operations 550, 560 and 570:

Operation 550: Variation of patient's airway pressure $\Delta Paw_{Vt_{PBW}}$ for the determined nominal tidal volume $Vt_{PBW}$ is estimated using equation (8):

$$\Delta Paw_{Vt_{PBW}} = Vt_{PBW} \cdot \frac{NME}{NVE} = Vt_{PBW} \cdot \frac{EAmsi}{Vt} \cdot \frac{\Delta Paw_{occ}}{EAmsi_{occ}} \quad (8)$$

Operation 560: A variation of patient's airway pressure $\Delta Paw_{EAmsi_{tgt}}$ for the target electrical activity $EAmsi_{tgt}$ of the patient's respiratory muscle is estimated using equation (9):

$$\Delta Paw_{EAmsi_{tgt}} = EAmsi_{tgt} \cdot NME = EAmsi_{tgt} \cdot \frac{\Delta Paw_{occ}}{EAmsi_{occ}} \quad (9)$$

Operation 570: The total ventilatory requirement $Req_{total}$ of the patient is estimated using equation (10):

$$Req_{total} = \frac{\Delta Paw_{VtPBW}}{\Delta Paw_{EAmsi\_tgt}} \cdot NME \quad (10)$$

As can be appreciated, in the above examples, the level of ventilatory assist to the patient ASSIST may be adjusted to compensate for a difference between $EAmsi_{Vt_{PBW}}$ and $EAmsi_{tgt}$, or between $\Delta Paw_{Vt_{PBW}}$ and $\Delta Paw_{Emsdi_{tgt}}$.

Figure 6:
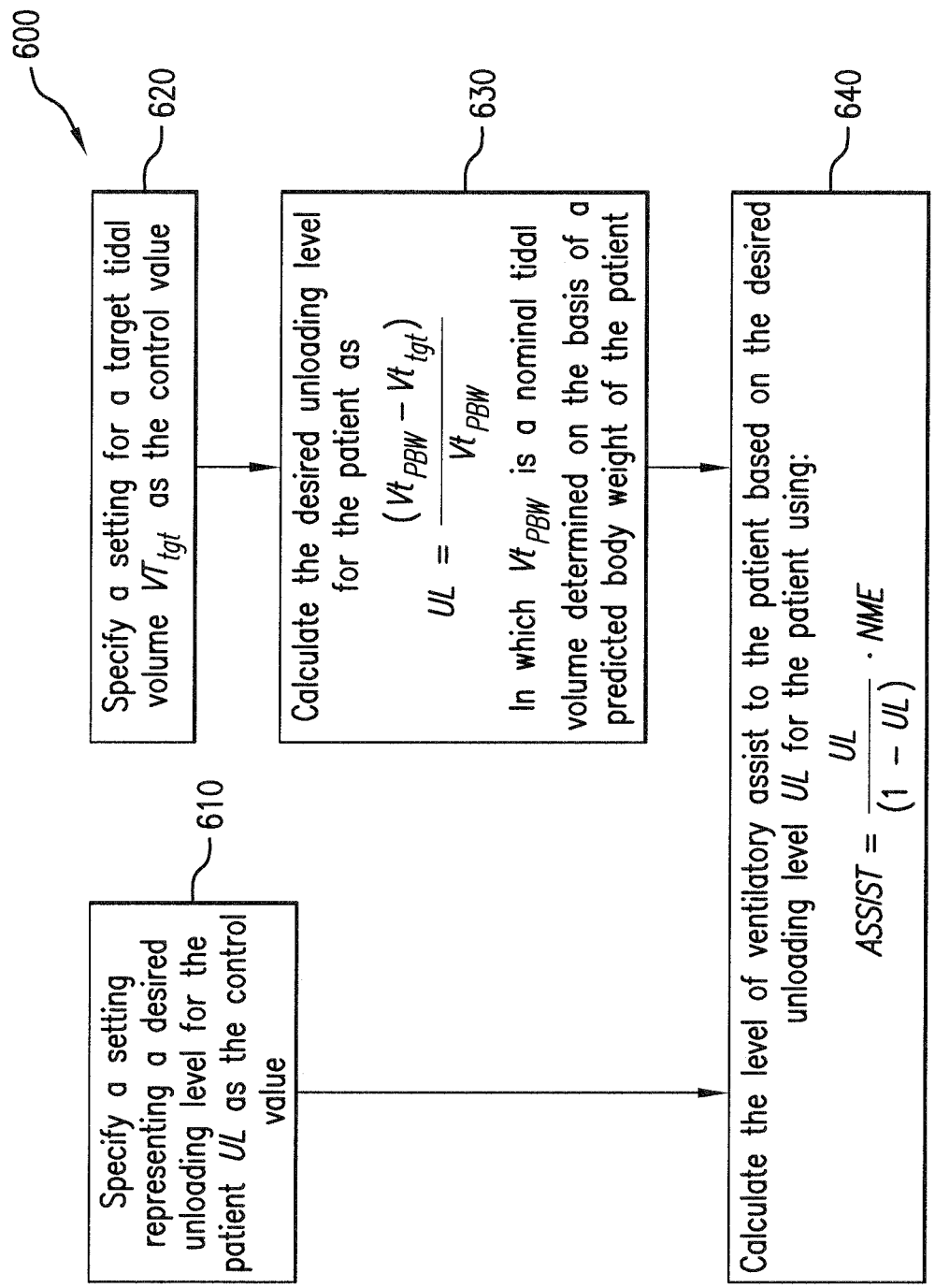
FIG. 6 illustrates a flow chart showing operations of a second method implemented in a mechanical ventilation system for calculating the level of ventilatory assist to the patient.

In a variant, the level of ventilatory assist to the patient ASSIST may be determined according to other operator defined parameters. FIG. 6 illustrates a flow chart showing operations of a second method implemented in a mechanical ventilation system for calculating the level of ventilatory assist to the patient. The flow chart of FIG. 6 includes a sequence 600 comprising a plurality of operations that may be executed in variable order, some of the operations possibly being executed concurrently, some of the operations being optional. The sequence 600 comprises the following operations:

Operation 610: A setting representing a desired unloading level UL for the patient is specified as the value mentioned in the description of Operation 110, which is the control value.

Operation 620: As an alternative to operation 610, a setting for a target tidal volume for the patient $Vt_{tgt}$ is specified as the control value.

Operation 630: Following operation 610, the desired unloading value is calculated using equation (11):

$$UL = \frac{(Vt_{PBW} - Vt_{tgt})}{Vt_{PBW}} \quad (11)$$

Operation 640: Whether the desired unloading level UL for the patient is obtained through Operation 610 or through Operations 620 and 630, the level of ventilatory assist to the patient is determined using equation (12):

$$ASSIST = \frac{UL}{(1-UL)} \cdot NME \quad (12)$$

It may be observed that the total ventilatory requirement $Req_{total}$ of the patient is not calculated in the sequence 600. However, the total ventilatory requirement $Req_{total}$ of the patient may be derived from the desired unloading value using equation (13):

$$Req_{total} = \left(\frac{UL}{(1-UL)} + 1\right) \cdot NME \quad (13)$$

Figure 7:
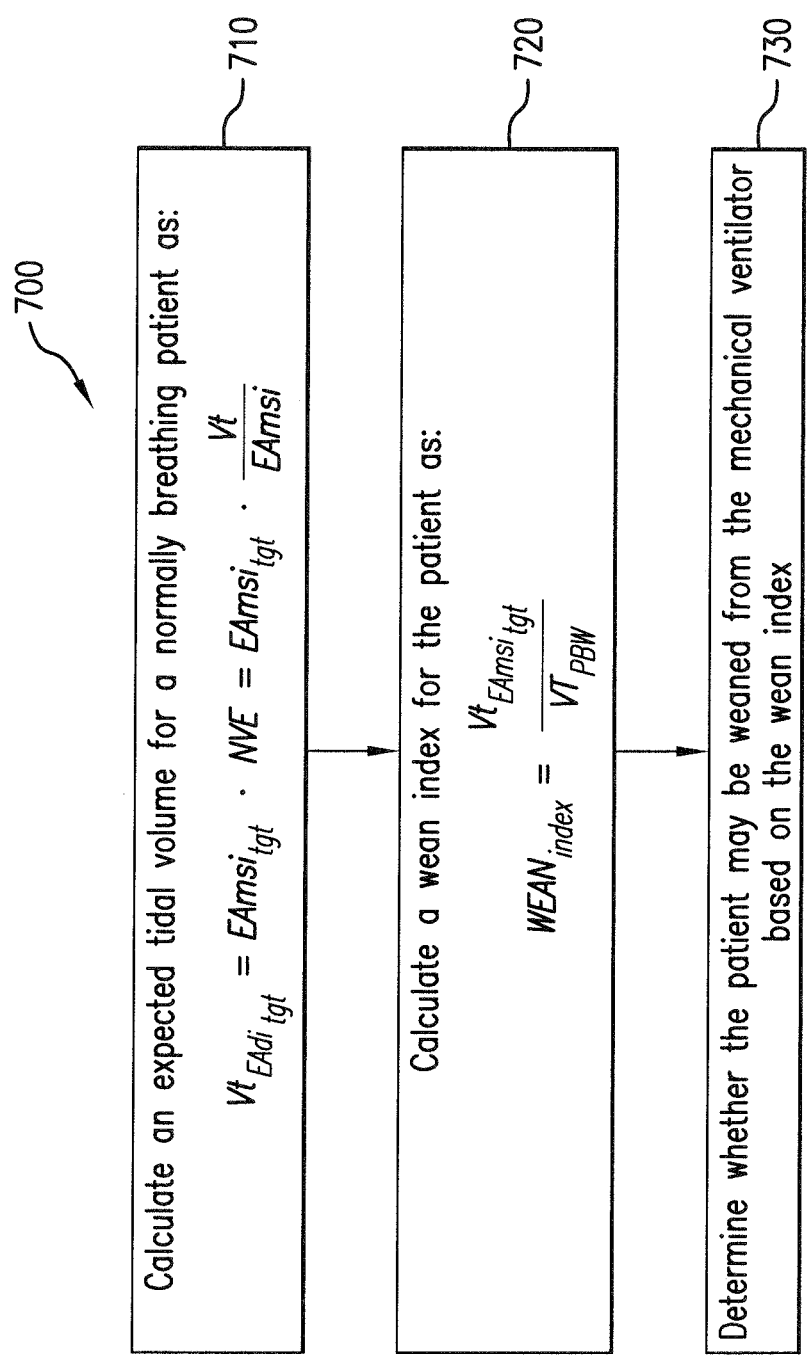
FIG. 7 illustrates a flow chart showing operations of a method implemented in a mechanical ventilation system for determining whether the patient may be weaned from the mechanical ventilator.

It may be desired to determine when the patient will be able to breathe normally without ventilatory assist. FIG. 7 illustrates a flow chart showing operations of a method implemented in a mechanical ventilation system for determining whether the patient may be weaned from the mechanical ventilator. The flow chart of FIG. 7 includes a sequence 700 comprising a plurality of operations that may be executed in variable order, some of the operations possibly being executed concurrently, some of the operations being optional. The sequence 700 comprises the following operations:

Operation 710: An expected tidal volume $Vt_{EAmsi_{tgt}}$ for a normally breathing patient may be obtained using equation (14):

$$Vt_{EAmsi_{tgt}} = EAmsi_{tgt} \cdot NVE = EAmsi_{tgt} \cdot \frac{Vt}{EAmsi} \quad (14)$$

Operation 720: In turn, a wean index is calculated at using equation (15):

$$WEAN_{index} = \frac{Vt_{EAmsi_{tgt}}}{Vt_{PBW}} \quad (15)$$

Operation 730: A determination is made at operation 170 that the patient may be deemed to be breathing normally when the $WEAN_{index}$ is about equal to 1, for example and without limitation when the $WEAN_{index}$ is at least 0.95 or in a range between 0.95 and 1.05.

Figure 8:
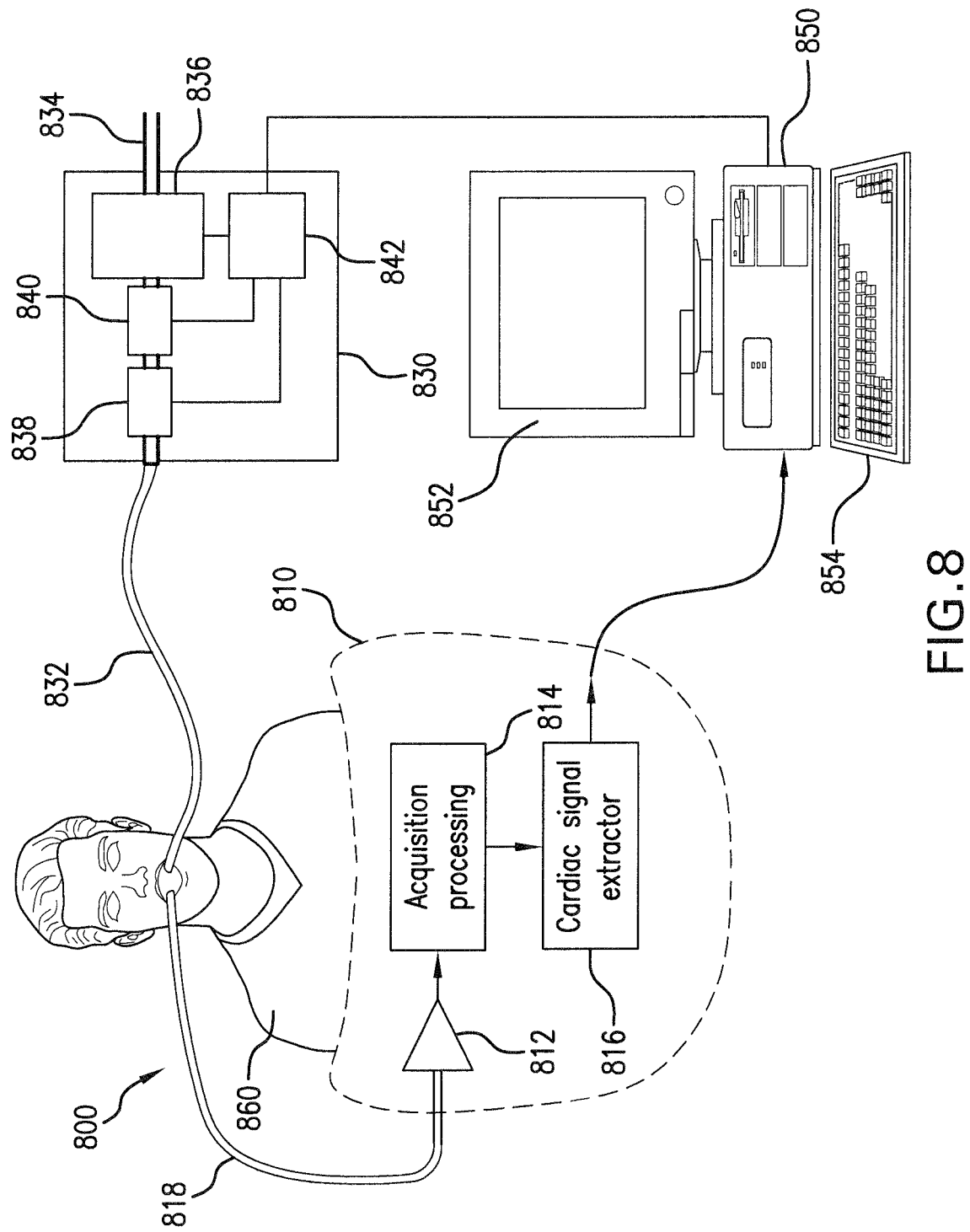
FIG. 8 is a block diagram of a mechanical ventilation system for determining and adjusting a level of ventilatory assist to a patient.

FIG. 8 is a block diagram of a mechanical ventilation system for determining and adjusting a level of ventilatory assist to a patient. A mechanical ventilation system 800 includes a signal acquisition unit 810, a mechanical ventilator 830 and a computer 850.

The signal acquisition unit 810 includes at least one sensor (not explicitly shown) placed on the body of a patient 860 and connected to an amplifier 812 via a cable 818 or via a wireless connection (not shown). The signal acquisition unit 810 also includes several processing modules (or analog components having the same functions) that are described hereinbelow.

The sensor is configured to measure electrical activity of a patient's respiratory muscle during an inspiratory effort of the patient 860. The sensor may be supported by an oesophageal catheter (shown in FIG. 9). The sensor may alternatively include one or more non-invasive sensors. International Patent Publication No. WO 2015/089668 A1 to Sinderby et al. (Sinderby '668), published on Jun. 25, 2015 and its corresponding U.S. patent application Ser. No. 15/105,613, filed on Jun. 6, 2016, the full disclosures of which being incorporated by reference herein, provide examples of non-invasive sensors that may be used to measure electrical activity of a patient's respiratory muscle or muscles during an inspiratory effort of the patient. International Patent Application No. PCT/SE2015/050369 to Jalde (Jalde '369), the full disclosure of which is incorporated by reference herein, discusses both invasive and non-invasive techniques for detection of electromyographic activity (EMG) at the level of the laryngopharyngeal region of a patient for control of a mechanical ventilator. Invasive measurements, obtained for example via an oesophagus catheter, and non-invasive measurements, obtained for example via a set of surface electrodes configured to be attached to the skin of the patient's neck, in particular to the area around the throat of the patient, may both be used to measure the inspiratory effort of the patient 860.

Being amplified by the amplifier 812, signal(s) from the sensor(s) indicative of the measured electrical activity are supplied to an acquisition processing module 814. The acquisition processing module 814 forwards the measured electrical activity representative signal(s) to an optional cardiac signal extractor 816 that, if present, removes cardiac signal components from the measured, electrical activity representative signal(s). As well known to those of ordinary skill in the art, to remove the cardiac signal components, the measured electrical activity representative signal(s) may be processed through an appropriately designed filter (not shown). The cardiac signal extractor 816 may also be designed to provide an indication, for example to an operator or to a caregiver, that cardiac signal components have not been properly detected in the measured electrical activity representative signal(s). In this respect, the cardiac signal components may be detected by sensing the high amplitude peak of the QRS complex.

The electrical signal acquisition unit 810 may include one or more of a filter, an integrator, a rectifier and an averager of the measured electrical activity representative signal(s). The signal acquisition unit 810 may further include an extractor operative to remove from the measured electrical activity representative signal(s) artifacts caused by electrical activity of patient's muscles not participating in the inspiratory effort of the patient. For example, without limitation, these elements may be made part of the acquisition processing module 814.

In an embodiment, some of the modules of the signal acquisition unit 810 may be integrated within a purpose-built device while some other modules of the signal acquisition unit 810 may be integrated within a generic computer.

Resulting electrical activity representative signal(s) from which the cardiac signal components have optionally been extracted are output from the signal acquisition unit 810 and supplied to the computer 850.

The mechanical ventilator 830 provides ventilatory assist to the patient via a breathing tube 832 connected between the mechanical ventilator 830 and the patient's airway. In a non-limitative example, the mechanical ventilator 830 includes a gas connection 834 coupled to a gas source (not shown) and supplying gas under pressure, such as air, oxygen, or any suitable breathing gas or mixture of gases, to a valve unit 836. The valve unit 836 comprises inspiratory and expiratory valves (not shown) for controlling pressure and flow of the breathing gas. The breathing gas is output from the valve unit 836 via the breathing tube 832 on which a pressure sensor 838 and a flow sensor 840 are mounted. The valve unit 836 is controlled by a control unit 842, and the pressure sensor 838 and the flow sensor 840 are connected to the control unit 842. A more detailed, non-limitative example of a mechanical ventilator is described in European Patent No. 1 896 102 B1 to Blomberg et al. issued on Feb. 1, 2012 and its corresponding U.S. Pat. No. 9,220,857 B2, issued on Dec. 29, 2015, the full disclosure of which are incorporated by reference herein.

The breathing tube 832 may be attached to an endotracheal tube (not shown) insertable in the trachea of the patient 860, or may be attached to a mask (not shown) that can be placed on the face of the patient 860.

The computer 850 acts as a controller of the mechanical ventilator 830. The computer 850 may be an external component or may alternatively be integrated within the mechanical ventilator 830 as a part of the control unit 842. Regardless, the computer 850 provides an interface between the signal acquisition unit 810 and the mechanical ventilator 830. The computer 850 may be connected to a monitor 852 to display, in particular but not exclusively, the various measurements obtained through the signal acquisition unit 810, the flow sensor 840 and the pressure sensor 838. The monitor 852 may further display one or more of the parameters calculated using some or all of equations (1) to (16). The computer 850 may also be connected to an operator interface 854, such as for example a keyboard. Alternatively, the monitor 852 and the keyboard may be substituted by or supplemented with a touch sensitive screen (not specifically shown) displaying a graphical user interface acting at once as the monitor 852 and the operator interface 854. The computer 850 may communicate individually, by wire or wirelessly, with any one of the modules of the signal acquisition unit 810.

Figure 9:
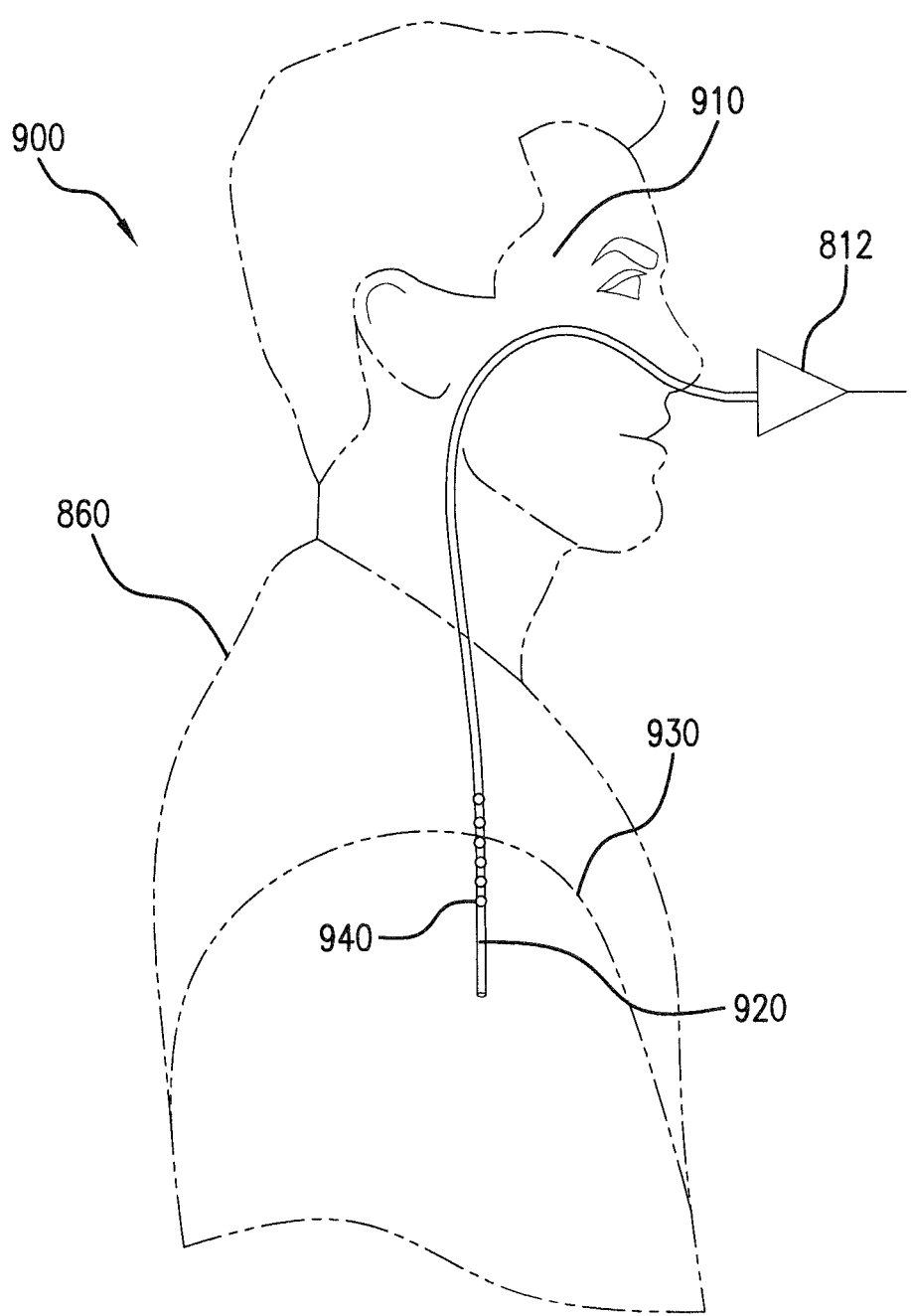
FIG. 9 is a schematic representation of a set-up for measuring electrical activity of a patient's respiratory muscle, for example the patient's diaphragm.

In an embodiment using as the patient's respiratory muscle the diaphragm of the patient, the electrical activity representative signal(s) reflect an electromyographic activity (EMG) of the diaphragm of the patient. The EMG signal may be obtained using any one of known techniques, including those taught in Sinderby '668 and in Jalde '369. FIG. 9 is a schematic representation of a set-up for measuring electrical activity of a patient's respiratory muscle, for example the patient's diaphragm. In a set up 900, an oesophageal catheter 910 is introduced into the oesophagus of the patient 860, through one nostril or through the mouth, until a free end section 920 of the oesophageal catheter 910 reaches the area of the diaphragm 930. A linear array of annular electrodes such as 940 mounted on the free end section 920 of the oesophageal catheter 910 is positioned at the level of the gastroesophageal junction. Electric wires (not shown) interconnect respective electrodes 940 to the amplifier 812 of FIG. 8. These electric wires follow the catheter 910 from the electrodes 940 to the amplifier 812, for example running through a lumen or lumens of the catheter 910. The electrodes such as 940 sense respective electric signals from the patient's diaphragm 930. These electric signals are supplied to the amplifier 812 through the electric wires (not shown) and are then amplified by this amplifier 812.

Details of an implementation of an oesophageal catheter such as 910 and the processing of the electric signals detected through the electrodes such as 940 are described in U.S. Pat. No. 5,671,752 to Sinderby et al., issued on Sep. 30, 1997, the full disclosure of which is incorporated by reference herein. From the teaching of this reference, it is believed to be within the capacity of those of ordinary skill in the art to construct a suitable oesophageal catheter such as 910 and to process the electric signals detected through annular electrodes such as 940 to provide an electrical activity representative signal. Accordingly, the oesophageal catheter 910 will not be further described in the present disclosure.

Returning to FIG. 8, for any type of sensor used to obtain measured electrical activity representative signal(s), the mechanical ventilation system 800 can be used for determining and/or adjusting a level of ventilatory assist to a patient ASSIST as follows.

To measure the values $\Delta Paw_{occ}$ and $EAmsi_{occ}$, the computer 850 and/or the control unit 842 close the inspiratory valve of the valve unit 836 to cause patient's inspiratory occlusion. Then, the pressure sensor 838 measures the patient's inspiratory pressure during a patient's unassisted inspiration attempt and the computer '850 and/or control unit 842 determine the variation of patient's inspiratory pressure $\Delta Paw_{occ}$ during the patient's unassisted inspiration attempt with patient's inspiratory occlusion. Concurrently, the signal acquisition unit 810 measures electrical activity of the patient's respiratory muscle during the patient's unassisted inspiration attempt with patient's inspiratory occlusion, and supplies the measured electrical activity representative signal(s) $EAmsi_{occ}$ to the computer 850

To measure the values Vt and EAmsi, the computer 850 and/or control unit 842 control the valves of unit 836 to cause a patient's unassisted inspiration without patient's inspiratory occlusion. The flow meter 840 measures the flow of gas through the breathing tube 832 and this flow measurement is integrated by the computer 850 and/or control unit 842 to provide the patient's inspiratory volume Vt during the patient's unassisted inspiration without patient's inspiratory occlusion. The signal acquisition unit 810 measures the electrical activity of the patient's respiratory muscle during the patient's unassisted inspiration without patient's inspiratory occlusion, and supplies the measured electrical activity representative signal EAmsi to the computer 850.

Components of the mechanical ventilation system 800, such as the inspiratory valve of the valve unit 836, the pressure sensor 838, the signal acquisition unit 810, and the computer 850 and/or control unit 842 implement a detector of the neuro-mechanical efficiency NME of the patient. Specifically, the computer 850 and/or control unit 842 calculate the NME using equation (1) from the measured pressure variation $\Delta Paw_{occ}$ and the measured electrical activity representative signal(s) $EAmsi_{occ}$.

The computer 850 and/or the control unit 842 also implement a controller of the mechanical ventilation system 800. Generally speaking, the controller of the mechanical ventilation system 800 is configured to perform the calculations of equations (1) to (16), or a subset thereof, based on the specifics of a particular application. As an example, the controller receives from the operator interface a control value and the neuro-mechanical efficiency ME. Based on these inputs, the controller determines the level of ventilatory assist to the patient ASSIST.

In one variant, the computer 850 and/or the control unit 842 cause the monitor 852 to display the determined level of ventilatory assist to the patient ASSIST as a suggested setting. The operator interface 854, in turn, may be configured to receive a command for manually adjusting the mechanical ventilation system. In another variant, the computer 850 and/or the control unit 842 may automatically adjust mechanical ventilation system according to the determined level of ventilatory assist to the patient ASSIST. In yet another variant, the computer 850 and/or the control unit 842 may cause the operator interface 854 to display the level of ventilatory assist to the patient ASSIST while automatically adjusting the mechanical ventilation system. In a further variant, the operator interface 854 may be used to select one of manual and automatic adjustment modes for the mechanical ventilation system.

In an embodiment, a sensor or a combination of sensors may obtain from the patient a measurement of a type that corresponds to a type of the control value. For example, where the control value comprises an airway pressure value, the sensor or sensors may provide a corresponding airway pressure value. The computer 850 and/or the control unit 842 may calculate a deviation between the control value and the measurement and recalculate the level of ventilatory assist to the patient ASSIST based on the control value, on the neuro-mechanical efficiency NME and on the deviation.

In the same or another embodiment, the computer 850 and/or the control unit 842 may calculate a total ventilatory requirement of the patient $Req_{total}$ using one of equations (7) or (10) and determine the level of ventilatory assist to the patient ASSIST using equation (3).

To use equation (7) in determining the total ventilatory requirement of the patient $Req_{total}$:
A neuro-ventilatory efficiency NVE of the patient is calculated using equation (4);
A nominal tidal volume $Vt_{PBW}$ is determined using a predicted body weight PBW of the patient. As described hereinabove, the predicted body weight PBW may be determined by the controller (computer 850 and/or control unit 842) based on a gender and a height of the patient, using well-know calculation methods and/or data tables stored in a memory of the computer 850. For example, the gender and height of the patient may be, for example, entered by a medical practitioner using the operator interface 854. A value for the PBW may also be directly entered on the operator interface 854. The computer can then determine the nominal tidal volume $Vt_{PBW}$ by multiplying the PBW by a constant, for example 6 ml per kg of PBW.
An expected electrical activity $EAmsi_{Vt_{PBW}}$ is estimated by the controller (computer 850 and/or control unit 842) using equation (5); and
The constant $EAmsi_{tgt}$ representative of the electrical activity of the patient's respiratory muscle synchronized with patient's inspiratory effort for a normally breathing patient is used. As indicated hereinabove, this constant is, for example, 10 µV when the patient's respiratory muscle is the diaphragm.

To use equation (10) in determining the total ventilatory requirement of the patient $Req_{total}$, the following terms are further determined:
The controller (computer 850 and/or control unit 842) estimates a variation of the patient's airway pressure $\Delta Paw_{Vt_{PBW}}$ for the determined nominal tidal volume $Vt_{PBW}$ using equation (8);
The controller (computer 850 and/or control unit 842) estimates a variation of the patient's airway pressure $\Delta Paw_{EAmsi_{tgt}}$ for the target electrical activity $EAmsi_{tgt}$ of the patient's respiratory muscle using equation (9).

The controller (computer 850 and/or control unit 842) then has all necessary parameters for computing the level of ventilatory assist ASSIST. The controller (computer 850 and/or control unit 842) may control the mechanical ventilator 830 to adjust the level of ventilatory assist to the patient to the value of this parameter ASSIST.

In another embodiment, the computer 850 and/or the control unit 842 may determine the level of ventilatory assist to the patient ASSIST on the desired unloading level UL using equation (12).

In order to determine when the patient will be able to breathe without ventilatory assist, the controller (computer 850 and/or control unit 842) estimates an expected tidal volume for a normally breathing patient using equation (14), following which the controller (computer 850 and/or control unit 842) calculate a wean index $WEAN_{index}$ using equation (15).

The mechanical ventilation system 800, specifically the controller (computer 850 and/or control unit 842) may determine whether the patient is deemed to be breathing normally when the $WEAN_{index}$ is about equal to 1, for example and without limitation when the $WEAN_{index}$ is at least 0.95 or in a range between 0.95 and 1.05. An indication of the actual wean index $WEAN_{index}$ may be displayed on the monitor 852 connected to the computer 850. In a variant, the controller (computer 850 and/or control unit 842) may cause the monitor 852 to display one or more suggested actions for weaning of the patient or for continued ventilation support.

Those of ordinary skill in the art will realize that the description of the method and mechanical ventilation system for adjusting a level of ventilatory assist to a patient are illustrative only and are not intended to be in any way limiting. Other embodiments will readily suggest themselves to such persons with ordinary skill in the art having the benefit of the present disclosure. Furthermore, the disclosed method and system may be customized to offer valuable solutions to existing needs and problems of adjusting a level of ventilatory assist to a patient.

In the interest of clarity, not all of the routine features of the implementations of the method and system for adjusting a level of ventilatory assist to a patient are shown and described. It will, of course, be appreciated that in the development of any such actual implementation of the method and system, numerous implementation-specific decisions may need to be made in order to achieve the developer's specific goals, such as compliance with application-, system- and business-related constraints, and that these specific goals will vary from one implementation to another and from one developer to another. Moreover, it will be appreciated that a development effort might be complex and time-consuming, but would nevertheless be a routine undertaking of engineering for those of ordinary skill in the field of ventilatory assist systems having the benefit of the present disclosure.

In accordance with the present disclosure, the components, process steps, and/or data structures described herein may be implemented using various types of operating systems, computing platforms, network devices, computer programs, and/or general purpose machines. In addition, those of ordinary skill in the art will recognize that devices of a less general purpose nature, such as hardwired devices, field programmable gate arrays (FPGAs), application specific integrated circuits (ASICs), or the like, may also be used. Where a method comprising a series of process steps is implemented by a computer or a machine and those process steps may be stored as a series of instructions readable by the machine, they may be stored on a tangible medium or a storage device.

Systems and modules described herein may comprise software, firmware, hardware, or any combination(s) of software, firmware, or hardware suitable for the purposes described herein. Software and other modules may reside on servers, workstations, personal computers, computerized tablets, personal digital assistants (PDA), and other devices suitable for the purposes described herein. Software and other modules may be accessible via local memory, via a network, via a browser or other application or via other means suitable for the purposes described herein. Data structures described herein may comprise computer files, variables, programming arrays, programming structures, or any electronic information storage schemes or methods, or any combinations thereof, suitable for the purposes described herein.

The present disclosure has been described in the foregoing specification by means of non-restrictive illustrative embodiments provided as examples. These illustrative embodiments may be modified at will. The scope of the claims should not be limited by the embodiments set forth in the examples, but should be given the broadest interpretation consistent with the description as a whole.

What is claimed is:

1. A method implemented in a mechanical ventilation system for adjusting a level of ventilatory assist (ASSIST) to a patient, comprising:
   receiving at the mechanical ventilation system a control value selected from:
     a desired unloading level (UL) for the patient, and
     an operator setting for a target tidal volume for the patient ($Vt_{tgt}$), wherein a relation between the desired unloading level and the target tidal volume, for a nominal tidal volume ($Vt_{PBW}$) determined based on a predicted body weight of the patient, is defined as:

$$UL = \frac{(Vt_{PBW} - Vt_{tgt})}{Vt_{PBW}};$$

measuring an electrical activity (EAmsi, $EAmsi_{occ}$) of a patient's respiratory muscle synchronized with an inspiratory effort of the patient;
   determining a neuro-mechanical efficiency (NME) of the patient, wherein the neuro-mechanical efficiency (NME) is calculated at least in part based on a ratio of a respiratory volume or pressure induced by the patient's respiratory muscle over the measured electrical activity (EAmsi) of the patient's respiratory muscle; and
   determining the level of ventilatory assist (ASSIST) to the patient on the basis of the neuro-mechanical efficiency (NME) of the patient and of the desired unloading level (UL).

2. The method of claim 1, comprising displaying the determined level of ventilatory assist (ASSIST).

3. The method of claim 2, comprising receiving a command for adjusting the mechanical ventilation system.

4. The method of claim 1, comprising automatically adjusting the mechanical ventilation system to provide the level of ventilatory assist (ASSIST) to the patient.

5. The method of claim 1, wherein determining the neuro-mechanical efficiency (NME) of the patient comprises:
   measuring a variation of a patient's airway pressure ($\Delta Paw_{occ}$) during an unassisted inspiration attempt while causing a patient's inspiratory occlusion;
   measuring the electrical activity ($EAmsi_{occ}$) of the patient's respiratory muscle synchronized with the inspiratory effort of the patient during the unassisted inspiration attempt while causing the patient's inspiratory occlusion; and
   determining the neuro-mechanical efficiency (NME) as:

$$NME = \frac{\Delta Paw_{occ}}{EAmsi_{occ}}.$$

6. The method of claim 5, wherein the control value is selected from (i) an operator setting representing a target electrical activity of the patient's respiratory muscle synchronized with an inspiratory effort for a normally breathing patient ($EAmsi_{tgt}$) and (ii) an operator setting for a variation of the patient's airway pressure ($\Delta Paw_{EAmsi_{tgt}}$) for the target electrical activity wherein ($EAmsi_{tgt}$) is calculated as:

$$EAmsi_{tgt} = \frac{\Delta Paw_{EAmsi_{tgt}}}{NME}.$$

7. The method of claim 6, comprising calculating a total ventilatory requirement ($Req_{total}$) of the patient on the basis of the inspiratory effort for the normally breathing patient ($EAmsi_{tgt}$).

8. The method of claim 7, wherein the level of ventilatory assist (ASSIST) to the patient is determined using the relation:

$$ASSIST = Req_{total} - NME.$$

9. The method of claim 7, comprising:
measuring an inspiratory volume (Vt) of the patient during an unassisted inspiration;
measuring the electrical activity (EAmsi) of the patient's respiratory muscle synchronized with the inspiratory effort of the patient during the unassisted inspiration;
determining a neuro-ventilatory efficiency of the patient as:

$$NVE = \frac{Vt}{EAmsi}.$$

10. The method of claim 9, wherein determining the total ventilatory requirement ($Req_{total}$) of the patient comprises:
determining a nominal tidal volume ($Vt_{PBW}$) on the basis of a predicted body weight of the patient;
estimating an expected electrical activity ($EAmsi_{Vt_{PBW}}$) for the nominal tidal volume ($Vt_{PBW}$) as:

$$EAmsi_{Vt_{PBW}} = \frac{Vt_{PBW}}{NVE} = Vt_{PBW} \cdot \frac{EAmsi}{Vt};$$

and
estimating the total ventilatory requirement ($Req_{total}$) of the patient as:

$$Req_{total} = \frac{EAmsi_{Vt_{PBW}}}{EAmsi_{tgt}} \cdot NME.$$

11. The method of claim 10, wherein determining the nominal tidal volume ($Vt_{PBW}$) comprises:
specifying a gender of the patient;
specifying a height of the patient;
determining the predicted body weight (PBW) of the patient on the basis of the gender and height of the patient; and
determining the nominal tidal volume ($Vt_{PBW}$) by multiplying the predicted body weight (PBW) by a constant.

12. The method of claim 9, wherein the patient's respiratory muscle is a diaphragm of the patient.

13. The method of claim 1, wherein the level of ventilatory assist (ASSIST) to the patient is determined using the relation:

$$ASSIST = \frac{UL}{(1-UL)} \cdot NME.$$

14. The method of claim 1, comprising:
obtaining, from the patient, a measurement corresponding to the control value;
calculating a deviation between the control value and the measurement; and
recalculating the level of ventilatory assist (ASSIST) to the patient on the basis of the neuro-mechanical efficiency (NME) of the patient, of the control value and of the deviation.

15. The method of claim 1, wherein measuring the electrical activity (EAmsi, $EAmsi_{occ}$) of the patient's respiratory muscle synchronized with the inspiratory effort of the patient comprises removing cardiac signal components from a measured electrical activity representative signal.

16. A mechanical ventilation system for adjusting a level of ventilatory assist (ASSIST) to a patient, comprising:
an operator interface adapted to receive a control value selected from:
a desired unloading level (UL) for the patient, and
an operator setting for a target tidal volume for the patient ($Vt_{tgt}$), wherein a relation between the desired unloading level and the target tidal volume, for a nominal tidal volume ($Vt_{PBW}$) determined based on a predicted body weight of the patient, is defined as:

$$UL = \frac{(Vt_{PBW} - Vt_{tgt})}{Vt_{PBW}};$$

an electrical activity sensor adapted to measure an electrical activity (EAmsi $EAmsi_{occ}$) of a patient's respiratory muscle synchronized with an inspiratory effort of the patient;
a detector of a neuro-mechanical efficiency (NME) of the patient, wherein the detector calculates the neuro-mechanical efficiency (NME) at least in part based on a ratio of a respiratory volume or pressure induced by the patient's respiratory muscle over the measured electrical activity (EAmsi) of the patient's respiratory muscle; and
a controller of the level of ventilatory assist (ASSIST) to the patient responsive to the control value from the operator interface and to the neuro-mechanical efficiency (NME) from the detector to determine the level of ventilatory assist (ASSIST) to the patient on the basis of the neuro-mechanical efficiency (NME) and of the desired unloading level (UL).

17. The mechanical ventilation system of claim 16, comprising a display for displaying the determined level of ventilatory assist (ASSIST).

18. The mechanical ventilation system of claim 17, wherein the operator interface is adapted to receive a command for adjusting the mechanical ventilation system.

19. The mechanical ventilation system of claim 16, wherein the controller is adapted to automatically adjust the mechanical ventilation system to provide the level of ventilatory assist (ASSIST) to the patient.

20. The mechanical ventilation system of claim 16, comprising an inspiratory valve operatively connected to the controller and adapted to cause a patient's inspiratory occlusion, wherein the detector of the neuro-mechanical efficiency (NME) comprises:
a pressure sensor adapted to measure a variation of a patient's airway pressure ($\Delta Paw_{occ}$) during an unassisted inspiration attempt while the inspiratory valve causes a patient's inspiratory occlusion;
wherein the electrical activity sensor is further adapted to measure the electrical activity ($EAmsi_{occ}$) of the patient's respiratory muscle synchronized with the inspiratory effort of the patient during the unassisted inspiration attempt while the inspiratory valve causes the patient's inspiratory occlusion; and
wherein the controller is adapted to determine the neuro-mechanical efficiency (NME) using the relation:

$$NME = \frac{\Delta Paw_{occ}}{EAmsi_{occ}}.$$

21. The mechanical ventilation system of claim 16, wherein operator interface is adapted to receive the control value in a form selected from (i) an operator setting representing a target electrical activity of the patient's respiratory muscle synchronized with an inspiratory effort for a normally breathing patient ($EAmsi_{tgt}$) and (ii) an operator setting for a variation of the patient's airway pressure ($\Delta Paw_{EAmsi_{tgt}}$) for the target electrical activity wherein the controller is adapted to calculate the inspiratory effort for the normally breathing patient ($EAmsi_{tgt}$) as:

$$EAmsi_{tgt} = \frac{\Delta Paw_{EAmsi_{tgt}}}{NME}.$$

22. The mechanical ventilation system of claim 16, wherein the controller is adapted to calculate a total ventilatory requirement ($Req_{total}$) of the patient on the basis of the inspiratory effort for the normally breathing patient ($EAmsi_{tgt}$).

23. The mechanical ventilation system of claim 22, wherein controller is adapted to determine the level of ventilatory assist (ASSIST) to the patient using the relation:

ASSIST=$Req_{total}$−NME.

24. The mechanical ventilation system of claim 22, comprising:
 a flow meter operatively connected to the controller and adapted to measure, in cooperation with the controller, an inspiratory volume (Vt) of the patient during an unassisted inspiration;
 wherein the electrical activity sensor is further adapted to measure the electrical activity (EAmsi) of the patient's respiratory muscle synchronized with the inspiratory effort of the patient during the unassisted inspiration; and
 wherein the controller is adapted to determine a neuro-ventilatory efficiency of the patient using the relation:

$$NVE = \frac{Vt}{EAmsi}.$$

25. The mechanical ventilation system of claim 24, wherein, to determine the total ventilatory requirement ($Req_{total}$) of the patient, the controller is adapted to:
 determine a nominal tidal volume ($Vt_{PBW}$) on the basis of a predicted body weight of the patient;
 estimate an expected electrical activity ($EAmsi_{Vt_{PBW}}$) for the nominal tidal volume ($Vt_{PBW}$) using the relation:

$$EAmsi_{Vt_{PBW}} = \frac{Vt_{PBW}}{NVE} = Vt_{PBW} \cdot \frac{EAmsi}{Vt};$$

and
 estimate the total ventilatory requirement ($Req_{total}$) of the patient using the following relation:

$$Req_{total} = \frac{EAmsi_{Vt_{PBW}}}{EAmsi_{tgt}} \cdot NME.$$

26. The mechanical ventilation system of claim 25, wherein the operator interface is adapted to receive specifications of a gender and of a height of the patient, and wherein the controller is adapted to:
 determine the predicted body weight (PBW) of the patient on the basis of the gender and height of the patient; and
 determine the nominal tidal volume ($Vt_{PBW}$) by multiplying the predicted body weight (PBW) by a constant.

27. The mechanical ventilation system of claim 24, wherein the patient's respiratory muscle is a diaphragm of the patient.

28. The mechanical ventilation system of claim 16, wherein the controller is adapted to determine the level of ventilatory assist (ASSIST) to the patient using the relation:

$$ASSIST = \frac{UL}{(1-UL)} \cdot NME.$$

29. The mechanical ventilation system of claim 16, comprising:
 a sensor adapted to obtain, from the patient, a measurement corresponding to the control value;
 wherein the control is further adapted to calculate a deviation between the control value and the measurement, and to recalculate the level of ventilatory assist (ASSIST) to the patient on the basis of the neuromechanical efficiency (NME) of the patient, of the control value and of the deviation.

30. The mechanical ventilation system of claim 16, comprising a cardiac signal extractor adapted to remove cardiac signal components from an electrical activity representative signal measured by the electrical activity sensor to provide the measured electrical activity (EAmsi, $EAmsi_{occ}$) of the patient's respiratory muscle synchronized with the inspiratory effort of the patient.

31. A method implemented in a mechanical ventilation system for determining whether a patient is ready to be weaned from the mechanical ventilation system, comprising:
 receiving at the mechanical ventilation system a control value representing a target electrical activity of a respiratory muscle of a normally breathing patient ($EAmsi_{tgt}$), the respiratory muscle being synchronized with an inspiratory effort for the normally breathing patient;
 measuring an inspiratory volume (Vt) of the patient during an unassisted inspiration;
 measuring the electrical activity (EAmsi) of the patient's respiratory muscle synchronized with the inspiratory effort of the patient during the unassisted inspiration;
 determining a nominal tidal volume ($Vt_{PBW}$) on the basis of a predicted body weight of the patient;
 estimating an expected tidal volume for the normally breathing patient using the relation:

$$Vt_{EAmsi_{tgt}} = EAmsi_{tgt} \cdot \frac{Vt}{EAmsi};$$

calculating a wean index ($WEAN_{index}$) using the following relation:

$$WEAN_{index} = \frac{Vt_{EAmsi_{tgt}}}{Vt_{PBW}};$$

and
  determining whether the patient is ready to be weaned from the mechanical ventilation system as a function of a value of the ($WEAN_{index}$).

32. A mechanical ventilation system, comprising:
  an operator interface adapted to receive a control value representing a target electrical activity of a respiratory muscle of a normally breathing patient ($EAmsi_{tgt}$), the respiratory muscle being synchronized with an inspiratory effort for the normally breathing patient;
  a flow meter adapted to measure an inspiratory volume (Vt) of a patient during an unassisted inspiration;
  an electrical activity sensor adapted to measure an electrical activity (EAmsi) of the patient's respiratory muscle synchronized with an inspiratory effort of the patient during the unassisted inspiration;
  a controller operatively connected to the operator interface, the flow meter and the electrical activity sensor, the controller being configured to:
    determine a nominal tidal volume ($Vt_{PBW}$) on the basis of a predicted body weight of the patient;
    estimate an expected tidal volume for the normally breathing patient using the relation:

$$Vt_{EAmsi_{tgt}} = EAmsi_{tgt} \cdot \frac{Vt}{EAmsi};$$

calculate a wean index ($WEAN_{index}$) using the following relation:

$$WEAN_{index} = \frac{Vt_{EAmsi_{tgt}}}{Vt_{PBW}};$$

and
  determine whether the patient is ready to be weaned from the mechanical ventilation system as a function of a value of the wean index ($WEAN_{index}$).

* * * * *